United States Patent [19]

Renaud et al.

[11] Patent Number: 5,001,129
[45] Date of Patent: Mar. 19, 1991

[54] OXAZOLOQUINOLINE COMPOUNDS AND THERAPEUTIC APPLICATION THEREOF

[75] Inventors: Alain J. L. Renaud, Rueil Malmaison; Alain R. Schoofs; Jean-Marc M. Guiraudie, both of Paris; Denis M. Brochet, Saint Maur, all of France

[73] Assignee: Delalande S.A., Courbevoie, France

[21] Appl. No.: 283,704

[22] Filed: Dec. 13, 1988

[30] Foreign Application Priority Data

Dec. 21, 1987 [FR] France .................................. 87 17842
Nov. 22, 1988 [EP] European Pat. Off. ........ 88402923.2

[51] Int. Cl.$^5$ .................... A61K 31/47; C07D 513/04
[52] U.S. Cl. ....................................... 514/291; 546/89; 546/152; 546/176; 546/178; 546/180; 544/89; 540/476; 540/479; 540/593; 514/215; 514/230.2; 514/376; 548/217; 548/484
[58] Field of Search .......................... 546/89; 514/294

[56] References Cited

U.S. PATENT DOCUMENTS

| 3,565,900 | 2/1971 | Houlihan et al. | 546/89 |
| 4,064,247 | 12/1977 | Farge | 546/89 |
| 4,163,786 | 8/1979 | Harsanyi et al. | 514/291 |
| 4,387,098 | 7/1983 | Barnes | 546/85 |

FOREIGN PATENT DOCUMENTS 1278272 6/1972 United Kingdom .................. 546/85

OTHER PUBLICATIONS

Chem. Abstr., vol. 78, Entry 136028h, (1978), (Snoke).
Snoke et al., Jour. Het. Chem., 1973, pp. 99–101.
Chem. Abstr., vol. 88, Entry 37121n, (1978).
Chem. Abstr., vol. 83, Entry 58696, (1975).

Primary Examiner—Donald G. Daus
Attorney, Agent, or Firm—Finnegan, Henderson, Farabow, Garrett & Dunner

[57] ABSTRACT

The present invention relates to tricyclic carbamates copying with the formula

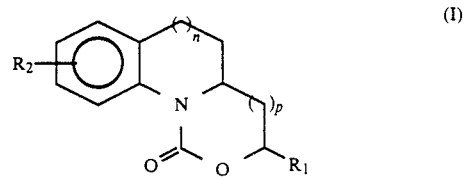

in which
n = 0, 1 or 2,
p = 0 or 1,
$R_1$ represents a hydrogen atom; a group which is alkyl in $C_1$–$C_4$; a phenyl group; a group which is alkenyl in $C_2$–$C_3$; or a methyl group substituted by a hydroxy group, a group which is alkoxy in $C_1$–$C_4$, an amino group or an N-alkylamino or N,N-dialkylamino group where the alkyl radical is in $C_1$–$C_4$, and
$R_2$ represents a hydrogen atom; a halogen atom; a group which is alkyl in $C_1$–$C_4$, or a group which is alkoxy in $C_1$–$C_4$, and their salts of addition of acid.

These compounds are therapeutically useful, notably as antidepressant agents.

8 Claims, No Drawings

OXAZOLOQUINOLINE COMPOUNDS AND THERAPEUTIC APPLICATION THEREOF

The present invention relates to novel tricyclic carbamates, a method of preparation and therapeutic application thereof, notably as antidepressant agents.

The tricyclic carbamates according to the invention comply more precisely with the formula

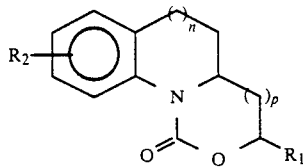

(I)

in which:
n = 0, 1 or 2,
p = 0 or 1, $R_1$ represents a hydrogen atom; a group which is alkyl in $C_1$-$C_4$; a phenyl group; a group which is alkenyl in $C_2$-$C_3$; or a methyl group substituted by a hydroxy group, a group which is alkoxy in $C_1$-$C_4$, an amino group or a N-alkylamino or N,N-dialkylamino group where the alkyl radical is in $C_1$-$C_4$, and $R_2$ represents a hydrogen atom; a halogen atom; a group which is alkyl in $C_1$-$C_4$; or a group which is alkoxy in $C_1$-$C_4$.

The present invention also relates to the salts of addition of mineral acid such as hydrochloric acid or organic acid such as a carboxylic acid, of the carbamates of formula (I) having a group which is salifiable by such an acid.

It should be noted that in the foregoing and hereafter the expression "alkyl in $C_1$-$C_4$" comprises groups with a straight or branched chain having up to 4 atoms of carbon, namely methyl, ethyl, n-propyl, i-propyl, n-butyl, i-butyl and tert-butyl; the expression "alkenyl in $C_2$-$C_3$" encompasses the vinyl, propenyl, i-propenyl and allyl groups; and the expression "alkoxy in $C_1$-$C_4$" complies with the formula -O-alkyl in $C_1$-$C_4$.

It will also be noted that the compounds of formula (I) have one or two asymmetric atoms of carbon depending on whether or not $R_1$ represents a hydrogen atom. Thus these compounds can exist in a certain number of stereoisomeric forms, including enantiomers. Thus the present invention extends to each of these stereoisomeric forms, including enantiomers, as well as mixtures thereof, including racemates.

The method of preparation of the tricyclic carbamates of formula (I) is characterised in that it includes (i) the cyclisation, by ethyl carbonate and in the presence of a base (for example an alcoholate of alkaline metal such as an alcoholate of sodium) or by phosgene, and preferably in an aprotic organic solvent such as toluene, of compounds of the formula

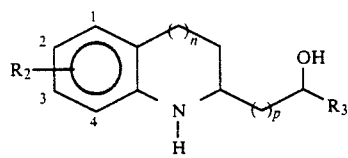

(II)

in which n, p and $R_2$ have the same significance as in formula (I) defined above and $R_3$ represents a hydrogen atom, a group which is alkyl in $C_1$-$C_4$, a group which is alkenyl in $C_2$-$C_3$ or a phenyl nucleus, or the intramolecular cyclisation in the presence of a base (for example an alcoholate of alkaline metal such as an alcoholate of sodium), and preferably in an aprotic organic solvent such as toluene, of compounds of the formula

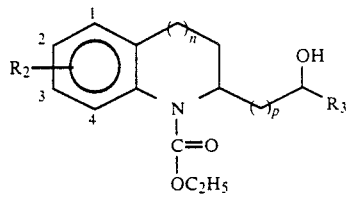

(III)

in which n, p, $R_2$ and $R_3$ have the same significance as in formula (II) above, which leads to compounds of the formula

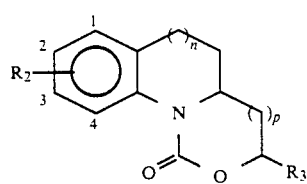

(Ia)

in which n, p, $R_2$ and $R_3$ have the same significance as in formula (II).

(ii) possibly ozonolysis of the compounds of formula (Ia) for which $R_3$ represents a $CH=CH_2$, this ozonolysis being followed by reduction preferably by a metal hydride, which leads to compounds of the formula

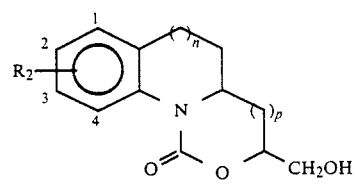

(Ib)

where n, p and $R_2$ have the same significance as in formula (Ia).

(iii) possibly the action of an alkylation agent, preferably a di(alkyl in $C_1$-$C_4$) sulphate, in the presence of a phase transfer catalyst such as tetrabutyl ammonium bromide, on the $CH_2OH$ radical of the compounds of formula (Ib) in order to obtain compounds of the formula

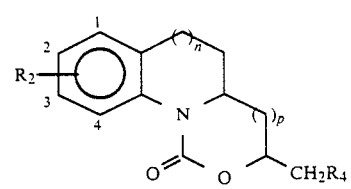

(Ic)

where n, p and $R_2$ have the same significance as in formula (Ib) and $R_4$ represents a group which is alkoxy in $C_1$-$C_4$, and (iv) possibly the action of a mesyl or tosyl halide on the compounds of formula (Ib), followed by the action either of sodium borohydride in dimethylsulphoxide, or of $NH_3$ or a mono- or dialkylamine of which the alkyl radical or radicals are in $C_1-C_4$, on the resulting mesylates or tosylates, which leads to compounds of the formula

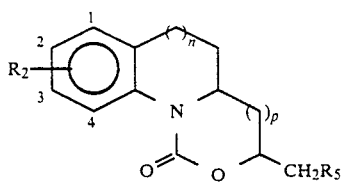
(Id)

where n, p and $R_2$ have the same significance as in formula (Ib) and $R_5$ represents a hydrogen atom, an amino group or an alkylamino or dialkylamino group of which the alkyl radical or radicals are in $C_1-C_4$.

The compounds of formula (II) are obtained (a) by the action of tert-butyllithium, preferably in an aprotic solvent (for example THF), on compounds of the formula

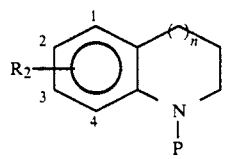
(IV)

in which n and $R_2$ have the same significance as in formula (I) and P represents a protective group of the nitrogen atom which is capable of activating the position in α of this nitrogen atom, (b) the action on the carbanion thus formed of an aldehyde of the formula $R_3CHO$ (V)

or an epoxy of the formula

(VI)

$R_3$ having in formulae (V) and (VI) the same significance as in formula (II), which leads to alcohols of the formula

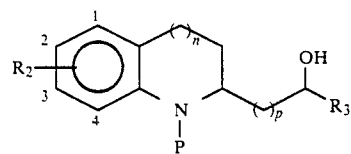
(VII)

where n, p, $R_2$ and $R_3$ have the same significance as in formula (II), then (c) the deprotection of these alcohols (VII).

Advantageously the protective group P has the formula

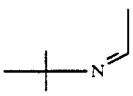

and in this case the deprotection is obtained by alkaline treatment in an alcoholic medium, by treatment with double hydride of lithium and aluminium in ether or by treatment with hydrazine in an alcoholic medium, which gives rise to compounds of the formula (II).

As regards the compounds of formula (IV), these are prepared in a known manner from corresponding indolins, tetrahydro-1,2,3,4 quinolines and tetrahydro-2,3,4,5 benzazepines. Thus, when P has the particular formula mentioned above, the protocol described by A. I. MEYERS, S. HEURING in Tetrahedron Lett., (1981), 22, 5119, can be put into effect.

The compounds of formula (III) for which $R_3$ represents a group which is alkyl in $C_1-C_4$, a group which is alkenyl in $C_2-C_3$ or a phenyl nucleus, are obtained by action of an organic magnesium or organic lithium compound in which the metal is bound to a group which is alkyl in $C_1-C_4$, a group which is alkenyl in $C_2-C_3$ or a phenyl nucleus, on compounds of the formula

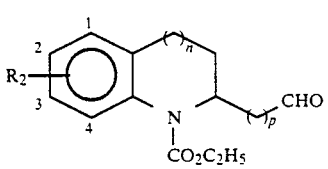
(VIII)

where n, p and $R_2$ have the same significance as in formula (I), followed by hydrolysis.

The compounds of formula (III) for which $R_3$ represents a hydrogen atom are obtained by reduction by hydrogen in the presence of a Pd/C catalyst of compounds of formula (VIII) defined above.

The compounds of formula (VIII) are obtained
(a) either by conversion by Raney nickel in the presence of sodium hypophosphite of tetrahydroquinolines of the formula

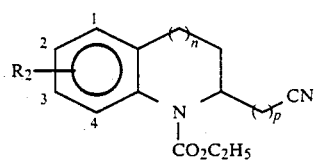
(IX)

where n, p and $R_2$ have the same significance as in formula (I), (b) or by oxidation by oxalyl chloride in the presence of DMSO and triethylamine of compounds of the formula

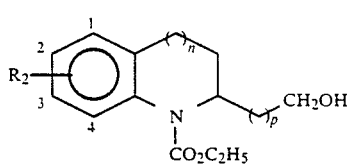
(X)

where n, p and $R_2$ have the same significance as in formula (I).

The compounds of formula (IX) for which p=0 and n=0, 1 or 2 are obtained by the action of trimethylsilyl cyanide in the presence of a Lewis acid such as $AlCl_3$ in an aprotic organic solvent such as dichloroethane on compounds of the formula

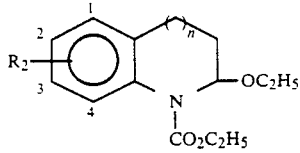
(XI)

where n and $R_2$ have the same significance as in formula (I).

The compounds of formula (IX) for which p=0 and n=1 can as a variant be obtained by hydrogenation in the presence of a hydrogenation catalyst such as palladium on barium sulphate or calcium carbonate of compounds of the formula

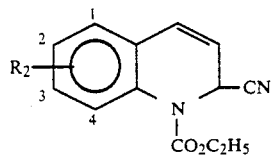
(XII)

where $R_2$ has the same significance as in formula (I), these compounds of formula (XII) being, for their part, obtained by the method described in Synthesis (1977), 497.

The compounds of formula (IX) for which p=1 and n=0, 1 or 2 are obtained by the action of a mesyl or tosyl halide on the compounds of formula (X) for which p=0, then subjecting the mesylates or tosylates thus obtained to the action of an alkaline metal cyanide such as sodium cyanide.

As regards the salts of the carbamates of formula (I), they are for example obtained by the action of a mineral or organic acid, in solution in an appropriate solvent, on a solution in an appropriate solvent of carbamates having a salifiable group, notably an amino, alkylamino or dialkylamino group.

Finally, it should be noted that the different stereoisomeric forms can be separated from one another by the usual methods and notably by liquid chromatography in particular on a column of silica.

The following preparations are given by way of examples to illustrate the invention.

EXAMPLE 1

(tert-butyliminomethyl)-1 methoxy-6 (hydroxy-3 propen-1 yl-3)-2 tetrahydro-1,2,3,4 quinoline [(VII), $R_2$=2-$OCH_3$, $R_3$: $CH=CH_2$, n=1, p=0].

The (tert-butyliminomethyl)-1 methoxy-6 tetrahydro-1,2,3,4 quinoline (50.5 g, 0.205 mole) is dissolved in 300 ml of tetrahydrofuran. The solution is cooled to −78° C. and the tert-butyllithium 1.7N in pentane (300 ml, 0.51 mole) is added drop by drop. The reaction medium is agitated for 1 h at a temperature of between −15° C. and −20° C. before being cooled again to −78° C. Acrolein (18 ml, 0.27 mole) in solution in 30 ml of tetrahydrofuran is added at this temperature. After 1 h of agitation, the medium is hydrolysed by the addition of 300 ml of water. After returning to ambient temperature, the medium is extracted with three times 300 ml of methylene chloride. The organic phases are collected, dried on sodium sulphate and evaporated. The product is utilised crude without any other purification in example 2.

EXAMPLE 2 methoxy-6 (hydroxy-3 propen-1 yl-3)-2 tetrahydro-1,2,3,4 quinoline [(II), $R_2$=2-$OCH_3$, $R_3$: $CH=CH_2$, n=1, p=0, code MD 280 402]

The crude product of example 1 is dissolved in 500 ml of methanol and a solution of potassium hydroxide 2N (1160 ml, 10 equivalents) is added. After 2 h of agitation to reflux of the solvent, the medium is extracted by two times 500 ml of methylene chloride. The product is extracted from the organic phases by two times 500 ml of a hydrochloric acid solution 3N, the aqueous phases obtained are alkalinised by a concentrated solution of sodium hydroxide and the product extracted by three times 500 ml of methylene chloride. After drying on sodium sulphate and evaporation of the solvent, 37 g of an oil was obtained which is purified on a column of alumina and eluted with isopropyl ether then with ethyl acetate.

$^1$H NMR ($CDCl_3$) δ in ppm: 6.5 (3H, broad singlet): 5.8 (1H, multiplet); 5.3 (2H, multiplet); 4.0 (1H, multiplet); 3.6 (3H, singlet); 3.0–3.4 (2H + 1H exchangeable); 2.6–2.9 (2H); 1.6 to 2.0 (2H).

In the same manner, but from appropriate starting materials, the other compounds of formula (II) are obtained, notably:

(hydroxy-3 propen-1 yl-3)-2 indolin [$R_2$=H, $R_3$: $CH=CH_2$, n=0, p=0, code: MD 200 599] in the form of oil.

$^1$H NMR ($CDCl_3$) δ in ppm: 2.5 (2H); 2.9 (2H); 3.6 to 4.2 (2H); 5 to 6.2 (3H); 6.4 to 7.2 (4H).

(hydroxy-3 propen-1 yl-3)-2 tetrahydro-1,2,3,4 quinoline [$R_2$=H, $R_3$: $CH=CH_2$, n=1, p=0, code: MD 200 501] in the form of oil.

$^1$H NMR ($CDCl_3$) δ in ppm: 1.6 to 2.2 (2H); 2.7 (2H); 3.2 (2H); 4 (2H); 5 to 5.2 (3H); 6.4 to 7.2 (4H).

EXAMPLE 3 ethenyl-3 methoxy-7 tetrahydro-3,3a, 4,5 1H-oxazolo [3.4-a] quinoline-one-1 [(Ia), $R_2$=2-$OCH_3$, $R_3$: $CH=CH_2$, n=1, p=0, cis, code: MD 280 403] and [(Ia), $R_2$=2-$OCH_3$, $R_3$: $CH=CH_2$, n=1, p=0, trans, code: MD 280 404]

The product of example 2 (10.5 g, 48 mmoles) is dissolved in 100 ml of toluene in the presence of diethyl carbonate (6.5 g, 55 mmoles). The medium is rendered anhydrous by azeotropic distillation of a part of toluene. The heat source is temporarily withdrawn and, at 100° C., a solution of sodium methylate 4N in methanol (1.2 ml, 4.8 mmoles) is added. The ethanol formed by the cyclisation reaction is distilled in azeotropic form with toluene towards 75°–78° C. When the temperature of the distillate reaches 110° C. the reaction is terminated. The solvent is evaporated in vacuo. The mixture of diastereoisomers obtained is then subjected to chromatography on silica using a n-heptane/ethyl acetate 70/30 eluent system.

The least polar product (MD 280 404) consisting of the racemic pair of diastereoisomers of trans relative configuration is eluted first: after evaporation of the elution solvents and recrystallisation in isopropyl ether, 2.9 g of this racemic is obtained.

The most polar product (MD 280 403) consisting of the racemic pair of diastereoisomers of cis relative configuration is eluted second: after evaporation of the solvents, 3.8 g (white solid) of this racemic is obtained.

EXAMPLE 4 cyano-2 dihydro-1,2 methyl-7 quinolinecarboxylate-1 of ethyl [(XII), $R_2=$3-$CH_3$, code: MD 370 236]

To a solution cooled to 0° C. of 0.6 mole (9.1 g) of methyl-7 quinoline in 110 ml of methylene chloride, 0.063 mole (8.5 ml) of trimethylsilyl cyanide is added in 5 minutes then in 5 minutes 0.063 mole (6.1 ml) of ethyl chloroformate and 0.44 g of aluminium chloride is added. After returning to ambient temperature, the reaction medium is poured onto water. The organic phase is washed with water, dried on sodium sulphate and concentrated. The product is purified by flash chromatography on silica (eluent: isopropyl ether/petroleum ether 50/50). 13.4 g of expected product is obtained, that is to say a yield of 87% (melting point 87° C.).

The following are obtained in the same way:

cyano-2 dihydro-1,2 methoxy-6 quinolinecarboxylate-1 of ethyl: [(XII), $R_2=$2-$OCH_3$, code: MD 280 523]; melting point=89° C.

cyano-2 dihydro-1,2 quinolinecarboxylate-1 of ethyl: [(XII), $R_2=$H, code: MD 280 441]; melting point=82° C.

chloro-7 cyano-2 dihydro-1,2 quinolinecarboxylate-1 of ethyl [(XII), $R_2=$2-Cl, code: MD 370 329]; oil.

EXAMPLE 5 cyano-2 tetrahydro-1,2,3,4 quinolinecarboxylate-1 of ethyl [(IX), $R_2=$H, n=1, p=0, code: MD 280 442]

Cyano-2 dihydro-1,2 quinolinecarboxylate-1 of ethyl (56.3 g, 0.24 mole) dissolved in 500 ml of methanol is subjected to hydrogenolysis under a pressure of 5 kg/$cm_2$ (approximately $5.10^5$ Pa) of hydrogen in the presence of 5% palladium on barium sulphate (5.6 g) at 40° C. for 2 h. The catalyst is eliminated by filtration, the solvent evaporated in vacuo and the residue crystallised in isopropyl ether. 48 g of a white solid corresponding to the expected product and having a melting point of 84° C. are obtained.

The following are obtained in the same way:

cyano-2 methyl-7 tetrahydro-1,2,3,4 quinolinecarboxylate-1 of ethyl [(IX), $R_2=$3-$CH_3$, n=1, p=0, code: MD 370 237]; yield=80%; melting point=110° C.

cyano-2 methoxy-6 tetrahydro-1,2,3,4 quinolinecarboxylate-1 of ethyl [(IX), $R_2=$2-$OCH_3$, n=1, p=0, code: MD 280 524]; yield=81%; melting point=80° C.

chloro-7 cyano-2 tetrahydro-1,2,3,4 quinolinecarboxylate-1 of ethyl [(IX) $R_2=$3-Cl, n=1, p=0, code: MD 370 330]; Yield=86%; melting point from 65° C.

EXAMPLE 6 ethoxy-2 tetrahydro-2,3,4,5 1H-benzazepinecarboxylate-1 of ethyl [(XI), $R_2=$H, n=2, code: MD 370 012]

A suspension of 0.31 mole (50 g) of tetrahydro-2,3,4,5 1H-benzazepine-one-2 in 250 ml of THF is added to a suspension of 16.9 g of NaH in 350 ml of THF, then the reaction medium is heated 1 h to reflux. The reaction medium is cooled to 40° C. and 0.62 mole (59.57 ml) of ethyl chloroformate is added, the temperature being maintained at 40° C., and heating is carried out to reflux 1 h. After cooling 20 ml of ethanol is added. The reaction medium is poured on ice. After extraction with ethyl ether 67% of ethoxycarbonyl-1 tetrahydro-2,3,4,5 1H-benzazepine-one-2 (melting point=74° C.) is obtained. A solution of 0.075 mole (17.5 g) of the latter in 300 ml of ethanol is cooled to −10° C. Bromocresol is added, then simultaneously 60 ml of hydrochloric ethanol and 0.225 ml of $NaBH_4$ (8.55 g), the pH being maintained at 5-6 and the temperature at −10° C. Then the temperature is allowed to rise to 20° C. and 20 ml of hydrochloric ethanol (3.1N) is added. After concentration the residue is poured on ice. The aqueous phase is extracted with ethyl ether. The organic phase is dried on sodium sulphate and concentrated. 17.2 g of product in the form of oil are obtained:

IR $\nu$ C=0: 1700 $cm^{-1}$.

$^1$H NMR ($CDCl_3$) $\delta$ ppm: 1 (3H); 1.2 (3H); 1.6-2 (4H); 2.6 (2H); 3.6 (2H); 4.2 (2H); 4-6 (1H); 7.1 (4H).

Ethoxy-2 methoxy-7 tetrahydro-2,3,4,5 1H-benzazepinecarboxylate-1 of ethyl [(XI), $R_2=$2-$OCH_3$, n=2, code: MD 370 245] is obtained in the same manner from corresponding starting materials:

IR $\nu$ C=0: 1700 $cm^{-1}$.

$^1$H NMR ($CDCl_3$) $\delta$ ppm: 1 (3H); 1.2 (3H); 1.6-2 (4H); 2.6 (2H); 3.6 (2H); 3.7 (3H); 4.2 (2H); 4.3 (1H); 6.6-7.1 (3H).

EXAMPLE 7 cyano-2 methoxy-7 tetrahydro-2,3,4,5 1H-benzazepinecarboxylate-1 of ethyl [(IX), $R_2=$2-$OCH_3$, n=2, p=0, code: MD 370 246]

0.392 mole (48.6 ml) of trimethylsilyl cyanide and 4.02 g of aluminium chloride are added at 15° C. to a solution of 0.3 mole (88.5 g) of ethoxy-2 methoxy-7 tetrahydro-2,3,4,5 1H-benzazepinecarboxylate-1 of ethyl [Code: MD 370 245] in 1 liter of methylene chloride. The temperature is allowed to rise to 20° C. and after 3 h of agitation the reaction medium is poured on iced water. The organic phase is washed with the water, dried on sodium sulphate and concentrated. The oil obtained is utilised immediately for the following stage.

Cyano-2 tetrahydro-2,3,4,5 1H-benzazepinecarboxylate-1 of ethyl [(IX), $R_2=$H, n=2, p=0, code: MD 370 013]

IR $\nu$ C≡N: 2240 $cm^{-1}$. $\nu$ C=0: 1700 $cm^{-1}$ is obtained in the same way.

EXAMPLE 8 carboxaldehyde-2 tetrahydro-1,2,3,4 quinolinecarboxylate-1 of ethyl [(VIII), $R_2=$H, n=1, p=0, code: MD 280 443]

The compound of example 5 (46 g, 0.2 mole) is dissolved in a medium containing acetic acid (330 ml), water (330 ml), pyridine (660 ml) and hydrated sodium hypophosphite (92 g). The solution is heated to 40° C. and Raney nickel (37 g) is added in small quantities in 5 to 6 hours. The catalyst is eliminated by filtration, the filtrate concentrated in vacuo. The residue is taken up by water, the product extracted by ether. The organic phase is washed with an aqueous solution saturated with ammonium chloride then dried on sodium sulphate. After evaporation of the solvent, distillation provides 36.4 g of the expected pure compound.

boiling point under 0.05 mm of Hg: 150° C., $^1$H NMR ($CDCl_3$) $\delta$ ppm: 1.3 (3H); 1.7 to 2.7 (4H); 4 to 4.5 (2H); 4.5 to 4.9 (1H); 6.9 to 7.5 (9H); 7.5 to 8.9 (1H); 9.6 (1H).

IR $\nu$ C=0: 1745, 1700 $cm^{-1}$.

The following compounds (VIII) are obtained in the same way from corresponding starting materials:

carboxaldehyde-2 chloro-7 tetrahydro-1,2,3,4 quinolinecarboxylate-1 of ethyl [$R_2$=3-Cl, n=1, p=0, code MD 370 331].

$^1$H NMR (CDCl$_3$) δ ppm: 1.3 (3H); 2 (2H); 2.6 (2H); 4.2 (2H); 4.7 (1H); 6.8–7.2 (2H); 7.8 (1H); 9.5 (1H).

IR ν C=0: 1753, 1710 and 1700 cm$^{-1}$.

carboxaldehyde-2 methoxy-6 tetrahydro-1,2,3,4 quinolinecarboxylate-1 of ethyl [$R_2$=2-OCH$_3$, n=1, p=0, code: MD 280 525].

$^1$H NMR (CDCl$_3$) δ ppm: 1.2 (3H); 1.8–2.3 (2H); 2.6 (2H); 3.7 (3H); 4.2 (2H); 4.7 (1H); 6.5–6.8 (2H); 7.6 (1H); 9.4 (1H).

IR ν C=0: 1740 and 1700 cm$^{-1}$.

carboxaldehyde-2 tetrahydro-2,3,4,5 1H-benzazepinecarboxylate-1 of ethyl [$R_2$=H, n=2, p=0, code: MD 370 014].

$^1$H NMR (CDCl$_3$) δ ppm: 1.2 (3H); 1.6–2 (2H); 2.7 (2H); 4.2 (2H); 4.8 (1H); 7–7.3 (4H); 9.5 (1H).

IR ν C=0: 1740 and 1700 cm$^{-1}$.

carboxaldehyde-2 methoxy-7 tetrahydro-2,3,4,5 1H-benzazepinecarboxylate-1 of ethyl [$R_2$=2-OCH$_3$, n=2, p=0, code: MD 370 247]

$^1$H NMR (CDCl$_3$) δ ppm: 1.2 (3H); 1.6–2.2 (4H); 2.7 (2H); 3.8 (3H); 4.2 (2H); 4.3 (1H); 6.6–6.8 (2H); 7.2 (1H); 9.3 (1H).

IR: ν C=0: 1740 and 1695 cm$^{-1}$.

EXAMPLE 9 ethoxycarbonyl-1 methoxy-6 tetrahydro-1,2,3,4 quinolineethanol-2 [(X), $R_2$=2-OCH$_3$, n=1, p=1, code: MD 370 315]

0.084 mole (1.8 g) of lithium borohydride is added little by little at 40° C. to a solution of 0.084 mole (19.4 g) [according to JOC, 16, p. 895 (1951)] of ethyl ester of methoxy-6 quinoline-2 acetic acid in 200 ml of dimethoxyethane. The reaction medium is heated 5 minutes to reflux. After cooling, the reaction medium is poured on water and the product is extracted by methylene chloride. After purification by chromatography on a column of silica (eluent: heptane-ethyl acetate 70/30) the product is recrystallised in isopropyl ether (yield=65%; melting point: 88° C.).

1.1 g of platinum oxide is added to a solution of 0.054 mole (11 g) of the previous product in 150 ml of methanol with several drops of hydrochloric ethanol (3N) and a stream of hydrogen is made to bubble therein for 12 h. After filtration, the organic phase is concentrated. The residue is taken up in methylene chloride. The organic phase is washed with an aqueous bicarbonate then with water, dried on sodium sulphate and concentrated. After purification by chromatography (eluent: heptane/ethyl acetate 40/60) 4.7 g of product are obtained in the form of oil. 0.0197 mole of this oil (4.1 g) is dissolved in 100 ml of chloroform to which is added 0.0394 mole (5.4 g) of potassium carbonate and 0.0237 mole (2.3 ml) of ethyl chloroformate. The reaction medium is heated to reflux for 2 h. After cooling, filtration and concentration, the residue is purified by chromatography on a column of silica (eluent: heptane/ethyl acetate 60/40). The expected product which is obtained is isolated with a yield of 80% in the form of oil.

$^1$H NMR (CDCl$_3$) δ ppm: 1.2 (3H); 1.4 to 1.8 (2H); 2 to 2.8 (4H); 3 to 3.7 (3H); 3.7 (3H); 4.2 (2H); 4.7 (1H); 6.5 to 6.8 (9H); 7.2 (1H)

IR:ν OH: 3450 cm$^{-1}$.

EXAMPLE 10 ethoxycarbonyl-1 methoxy-6 tetrahydro-1,2,3,4 quinoline-2 acetaldehyde [(VIII), $R_2$=2-OCH$_3$, n=1, p=1, code: MD 370 316]

0.0292 mole of DMSO in 16 ml of methylene chloride cooled to −60° C. is added to a solution of 0.016 mole (2 g) of oxalyl chloride in 26 ml of methylene chloride, then 0.0146 mole (4.1 g) of the compound obtained in example 9 is added in solution in 16 ml of methylene chloride. Then after 15 minutes 0.073 mole of triethylamine are added in solution in 16 ml of methylene chloride. The temperature is allowed to rise to +20° C. The reaction medium is concentrated to dryness and the residue is taken up in a water-methylene chloride mixture. The organic phase is washed with water, dried on sodium sulphate and concentrated. The expected product which is obtained is isolated in the form of oil after chromatography on a column of silica (eluent: heptane/ethyl acetate 90/10).

Yield: 69%.

IR:ν C=0: 1770 cm$^{-1}$ and 1745 cm$^{-1}$.

$^1$H NMR (CDCl$_3$) δ ppm: 1.2 (3H); 1.4 to 1.7 (2H); 2 to 2.8 (4H); 3.7 (3H); 4.2 (2H); 5 (1H); 6.5 to 6.8 (2H); 7.3 (1H); 9.5 (1H).

EXAMPLE 11 ethenyl-3 tetrahydro-3,3a,4,5 1H-oxazolo [3,4-a] quinoline-one-1 [(Ia), n=1, p=0, $R_2$=H, $R_3$=CH=CH$_2$, cis, code: MD 200 502] and [(Ia), n=1, p=0, $R_2$=H, $R_3$=CH=CH$_2$, trans, code: MD 200 503]

The magnesium vinyl bromide (0.165 mole) prepared from vinyl bromide (11.6 ml, 0.165 mole) and magnesium (3.86 g, 0.165 mole) in 80 ml of tetrahydrofuran is added drop by drop to a solution of the compound code MD 280 443 (prepared in example 8) in 350 ml of tetrahydrofuran, kept at a temperature between −20° C. and −40° C. The agitation is maintained ½ h after the end of the addition, then an aqueous solution saturated with ammonium chloride is introduced. The reaction medium is extracted with ethyl ether, the organic phase washed by an aqueous solution saturated with sodium chloride, dried by sodium sulphate, then evaporated in vacuo. The residue is taken up by 500 ml of toluene and treated as in example 3 by sodium methylate in order to achieve cyclisation. The toluene is then evaporated, the medium taken up by methylene chloride, washed with water, dried on sodium sulphate then evaporated. The mixture of two pairs of diastereoisomers obtained (32.6 g) is then separated by liquid chromatography on silica.

The least polar product (code: MD 200 503) is constituted by the racemic pair of diastereoisomers of trans relative configuration.

The most polar product (code: MD 200 502) is constituted by the racemic pair of diastereoisomers of cis relative configuration.

EXAMPLE 12 trans hydroxymethyl-3 tetrahydro-3,3a, 4,5 1H-oxazolo [3,4-a] quinoline-one-1 [(Ib), n=1, p=0, $R_2$=H, code: MD 200 505]

The trans product code MD 200 503 (2.5 g, 11.6 mmoles) is dissolved in a mixture of methanol (45 ml) and methylene chloride (35 ml). A stream of ozone is made to flow for 1 h through the solution cooled to −60° C. (rate of gas flow 0.8 l/mn containing 0.6M of ozone). The temperature of the reaction medium is then allowed to rise between −20° C. and −30° C. before the addition of sodium borohydride (7.4 g, 19.7 mmoles). After 30 agitation at this temperature, dimethylsulphide (11 ml, 15 mmoles) is added. The agitation is maintained 3 hours more and the medium is allowed to return to ambient temperature. The reaction medium is poured on a solution of hydrochloric acid 1N, the product is extracted by methylene chloride, the organic phase dried on sodium sulphate and evaporated in vacuo. After purification on a column of silica (eluent system n-heptane/ethyl acetate 20/80) 2.3 g of the pure expected product is obtained.

EXAMPLE 13 cis methoxymethyl-3 tetrahydro-3,3a,4,5 1H oxazolo [3,4-a] quinoline-one-1 [(Ic), $R_4=OCH_3$, $R_2=H$, n=1, p=0, code: MD 200 682]

The compound cis hydroxymethyl-3 tetrahydro-3,3a,4,5 1H-oxazolo [3,4-a] quinoline-one-1 [(Ib); code: MD 200 504] (5.6 g, 25.5 g mmoles) is put in suspension in 100 ml of toluene. To this suspension are added tetrabutyl ammonium bromide (820 mg. 2.5 mmoles), dimethylsulphate (7.2 ml, 76 mmoles), then a solution of sodium hydroxide at 50% (127 mmoles). The reaction medium is agitated during one night at ambient temperature, then water (100 ml) is added. The aqueous phase is decanted then extracted with toluene. The organic phases are collected, dried on sodium sulphate, then evaporated in vacuo. The residue is crystallised in an ethyl ether/petroleum ether mixture. Flash chromatography on silica (eluent: n-heptane/ethyl acetate 50/50) provides 4.3 g of the pure expected product.

EXAMPLE 14 methanesulphonate of cis methoxy-7 tetrahydro-3,3a,4,5 1H-oxazolo [3,4-a] quinoline-one-1 yl-3 methanol [code: MD 370 046]

0.026 mole (3.6 ml) of triethylamine and 0.026 mole (2 ml) of mesyl chloride are added to a suspension on cooled to 0° C. of 0.0224 mole (5.6 g) of cis hydroxymethyl-3 methoxy-7 tetrahydro-3,3a,4,5 1H-oxazino [3, 4a] quinoline-one-1 (code: MD 280 386) in 130 ml of methylene chloride. Then the reaction medium is left ½ hour at ambient temperature and poured on water. The organic phase is dried on sodium sulphate and concentrated. The expected product which is obtained is isolated with a yield of 97% (melting point=164° C.).

The methanesulphonate of trans methoxy-7 tetrahydro-3,3a,4,5 1H-oxazolo [3,4-a] quinoline-one-1 yl-3 methanol [code: MD 370 074] is obtained in the same way from corresponding starting materials.
Yield: 95%.
Melting point: 177° C.

EXAMPLE 15 trans methyl-3 tetrahydro-3,3a,4,5 1 H-oxazolo [3,4-a] quinoline-one-1 [(Id), $R_2=H$, n=1, p=0, $R_5=H$, code: MD 280 430]

$1.27.10^{-3}$ mole of tosyl chloride (0.24 g) at 0° C. is added to a solution of $0.9.10^{-3}$ (0.2 g) of the compound prepared in example 12, in 4 ml of pyridine. After 4 h of contact, the reaction medium is poured on iced water and the tosylate obtained is filtered (melting point=186° C.). $1.07.10^{-3}$ mole of sodium borohydride and $0.5.10^{-3}$ mole (0.2 g) of the preceding tosylate are added to 5 ml of DMSO and heated to 90° C. for 40 minutes. The reaction medium is poured on water and extracted with ethyl ether. The organic phase is dried on sodium sulphate and concentrated. The expected product which is obained is isolated with a yield of 72%.

EXAMPLE 16 cis aminomethyl-3 methoxy-7 tetrahydro-3,3a,4,5 1H-oxazolo [3,4-a] quinoline-one-2 [(Id), $R_2=2-OCH_3$, n=1, p=0, $R_5=NH_2$, code: MD 370 024]

A solution of 0.024 mole (6 g) of methanesulphonate of cis methoxy-7 tetrahydro-3,3a,4,5 1H-oxazolo [3,4-a] quinoline-one-1 yl-3 methanol [code: MD 370 046] in 40 ml of methanol and 20 ml of ethanol and 60 ml of liquid ammonia are placed in a pressure-resistant reactor. It is heated to 80° C. for 12 h: The reaction medium is concentrated and the residue is taken up in methylene chloride. The organic phase is washed in water and in aqueous ammonia, dried and concentrated. The expected product which is obtained is isolated in hydrochloride form with a yield of 20%.

Using the operational methods given above, but starting from appropriate reactants, the other compounds according to the invention are obtained. The physical characteristics of a certain number of compounds (I) are assembled in Table I which follows; it should be noted that the compounds listed in this Table occur in the form of racemic pair of diastereoisomers of cis or trans relative configuration.

TABLE I

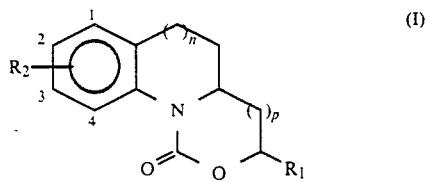

(I)

| Code | n | p | $R_2$ | $R_1$ | Configuration | Base or salt | Empirical formula | Mp (°C.) | NMR Nucleus | NMR Solvent | NMR δ p.p.m. | I.R. $\nu C=O$ $cm^{-1}$ |
|---|---|---|---|---|---|---|---|---|---|---|---|---|
| MD 200602 | 0 | 0 | H | $CH_2OH$ | cis | base | $C_{11}H_{11}NO_2$ | 128 | $^1H$ | DMSOd$_6$ | 2.8–3.4(2H); 3.7(2H); 4.7–5.2(3H); 6.8–7.4 (4H) | 1730 |
| MD 200718 | 0 | 0 | H | $CH_2OH$ | trans | base | $C_{11}H_{11}NO_3$ | 113 | $^1H$ | DMSOd$_6$ | 3–3.4(2H); 3.7(2H); 4.4–4.8(2H); 5.2(1H); 7–7.4(4H) | 1740 |
| MD | 0 | 0 | H | $CH=CH_2$ | cis | base | $C_{12}H_{11}NO_2$ | 74 | $^1H$ | CDCl$_3$ | 2.6–3.4(2H); 4.7–6.2 | 1750 |

TABLE I-continued

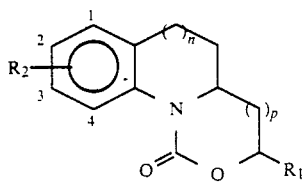
(I)

| Code | n | p | R₂ | R₁ | Configuration | Base or salt | Empirical formula | Mp (°C.) | NMR Nucleus | NMR Solvent | NMR δ p.p.m. | I.R. vC=O cm⁻¹ |
|---|---|---|---|---|---|---|---|---|---|---|---|---|
| MD 200601 | 0 | 0 | H | CH=CH₂ | trans | base | $C_{12}H_{11}NO_2$ | — | ¹H | CDCl₃ | 2.8–3.4(2H); 4.2–5 (2H); 5.2–6.4(3H); 6.8–7.4(4H) (5H): 6.8-7.4(4H) | 1760 |
| MD 200504 | 1 | 0 | H | CH₂OH | cis | base | $C_{12}H_{13}NO_3$ | 131 | ¹H | DMSOd₆ | 1.8–2.2(2H); 2.8(2H); 3.6(2H); 4–4.8(2H); 5 (1H); 6.8–7.3(3H); 8.1(1H) | 1700 |
| MD 200505 | 1 | 0 | H | CH₂OH | trans | base | $C_{12}H_{13}NO_3$ | 138 | ¹H | CDCl₃ | 1.5–2.2(2H); 2.8(2H); 3.7(2H); 4(1H); 4.3(1H); 5.2(1H); 6.8–7.3(3H); 8.1(1H) | 1720 |
| MD 200502 | 1 | 0 | H | CH=CH₂ | cis | base | $C_{13}H_{13}NO_2$ | 91 | ¹H | CDCl₃ | 1.6–2.2(2H); 2.8(2H); 3.9–4.3(1H); 4.8–6.2 (4H); 6.8–7.4(3H); 8.2(1H) | 1740 |
| MD 200503 | 1 | 0 | H | CH=CH₂ | trans | base | $C_{13}H_{13}NO_2$ | 121 | ¹H | CDCl₃ | 1.6–2.4(2H); 2.9(2H); 3.8(1H); 4.6(1H); 5.3–6.3(3H); 6.8–7.4(3H); 8.3(1H) | 1760 |
| MD 200682 | 1 | 0 | H | CH₂—OCH₃ | cis | base | $C_{13}H_{15}NO_3$ | 113 | ¹H | CDCl₃ | 1.6–2.2(2H); 2.8(2H); 3.4(3H); 3.6(2H); 4.4–4.8(2H); 6.8–7.2(3H); 8.1(1H) | 1740 |
| MD 200683 | 1 | 0 | H | CH₂—OCH₃ | trans | base | $C_{13}H_{15}NO_3$ | 69 | ¹H | CDCl₃ | 1.5–2.4(2H); 2.8(2H); 3.4(3H); 3.6(2H); 3.6–4.4(2H); 6.8–7.2(3H); 8.1(1H) | 1750 |
| MD 280389 | 1 | 0 | H | C₆H₅ | cis | base | $C_{17}H_{15}NO_2$ | 123 | ¹H | CDCl₃ | 1–1.8(2H); 2.8(2H); 4.2–4.6(1H); 5.7(1H); 7–7.4(8H); 8.2(1H) | 1740 |
| MD 280390 | 1 | 0 | H | C₆H₅ | trans | base | $C_{17}H_{15}NO_2$ | 135 | ¹H | CDCl₃ | 1.6–2.4(2H); 2.9(2H); 3.9(1H); 5.1(1H); 7–7.4 (3H); 8.3(1H) | 1750 |
| MD 280526 | 1 | 0 | H | H | — | base | $C_{11}H_{11}NO_2$ | 95 | ¹H | CDCl₃ | 1.1(3H); 1.5–2.2(4H); 2.8(2H); 3.9–4.7(2H); 8.1(1H) | 1750 |
| MD 280429 | 1 | 0 | H | CH₃ | cis | base | $C_{12}H_{13}NO_2$ | 114 | ¹H | CDCl₃ | 1.4(3H); 1.6–2.2(2H); 2.9(2H); 4.1(1H); 4.8 (1H); 6.8–7.4(3H); 8.2(1H) | 1730 |
| MD 280430 | 1 | 0 | H | CH₃ | trans | base | $C_{12}H_{13}NO_2$ | 128 | ¹H | CDCl₃ | 1.4(3H); 1.5–2.3(2H); 2.8(2H); 3.7(1H); 4.4(1H); 6.8–7.3(3H); 8.1(1H) | 1740 |
| MD 280460 | 1 | 0 | H | C₂H₅ | cis | base | $C_{13}H_{15}NO_2$ | 114 | ¹H | CDCl₃ | 1.1(3H); 1.6–2.3(4H); 2.9(2H); 3.6–4.4(2H); 6.8–7.4(3H); 8.2(1H) | 1750 |
| MD 280459 | 1 | 0 | H | C₂H₅ | trans | base | $C_{13}H_{15}NO_2$ | 96 | ¹H | CDCl₃ | 1.1(3H); 1.6–2.3(4H); 2.9(2H); 3.6–4.4(2H); 6.8–7.4(3H); 8.2(1H) | 1750 |
| MD 370030 | 1 | 0 | H | CH₂N—(CH₃)₂ | cis | salt HCl | $C_{14}H_{19}ClN_2O_2$ | >250 | ¹H | DMSOd₆ | 1.6–2.4(2H); 2.8(8H); 3.6(2H); 4.4(1H); 5.3(1H); 7–7.4(3H); 8(1H) | 1745 |
| MD 370031 | 1 | 0 | H | CH₂N—(CH₃)₂ | trans | salt HCl | $C_{14}H_{19}ClN_2O_2$ | >250 | ¹H | DMSOd₆ | 1.6–2.4(2H); 2.9(8H); 3.6(2H); 4(1H); 5(1H); 7–7.4(3H); 8.2(1H) | 1760 |
| MD 370032 | 1 | 0 | 3-CH₃ | CH₂OH | cis | base | $C_{13}H_{15}NO_3$ | 160 | ¹H | CDCl₃ | 2.1(2H); 2.3(3H); 2.9(2H); 3.8(3H); 4.3(1H); 4.7(1H); 6.8–7.2(2H); 8(1H) | 1715 |
| MD 370033 | 1 | 0 | 3-CH₃ | CH₂OH | trans | base | $C_{13}H_{15}NO_3$ | 139 | ¹H | CDCl₃ | 1.8–2.4(2H); 2.3(3H); 2.9(2H); 3.9(3H); 4.2(1H); 4.6(1H); 6.7–7.3(2H); 8(1H) | 1715 |

TABLE I-continued

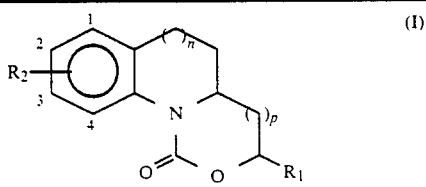
(I)

| Code | n | p | R₂ | R₁ | Configuration | Base or salt | Empirical formula | Mp (°C.) | NMR Nucleus | NMR Solvent | NMR δ p.p.m. | I.R. νC=O cm⁻¹ |
|---|---|---|---|---|---|---|---|---|---|---|---|---|
| MD 370336 | 1 | 0 | 3-Cl | CH₂OH | cis | base | C₁₂H₁₂ClNO₃ | 172 | ¹H | DMSOd₆ | 1.6–2.4(2H); 2.8(2H); 3.7(2H); 4–4.8(2H); 5.2(1H); 6.9–7.3(2H); 8.2(1H) | 1720 |
| MD 370335 | 1 | 0 | 3-Cl | CH₂OH | trans | base | C₁₂H₁₂ClNO₃ | 152 | ¹H | DMSOd₆ | 1.5–2.4(2H); 2.8(2H); 3.6–4.5(4H); 5.2(1H); 6.9–7.3(2H); 8.1(1H) | 1730 |
| MD 370038 | 1 | 1 | 2-OCH₃ | CH₂OH | most polar | base | C₁₄H₁₇NO₄ | 144 | ¹H | CDCl₃ | 1.7–2.6(5H); 2.9(2H); 3.8(6H); 4.5(1H); 6.6–6.8(2H); 7.8(1H) | 1720 |
| MD 370039 | 1 | 1 | 2-OCH₃ | CH₂OH | least polar | base | C₁₄H₁₇NO₄ | 177 | ¹H | CDCl₃ | 1.6–2.4(5H); 2.9(2H); 3.8(6H); 4.4(1H); 6.6–6.8(2H); 7.7(1H) | 1730 |
| MD 280403 | 1 | 0 | 2-OCH₃ | CH=CH₂ | cis | base | C₁₄H₁₅NO₃ | 100 | ¹H | CDCl₃ | 1.7–2.1(2H); 2.9(2H); 3.8(3H); 4.2(1H); 4.9–6(4H); 6.6–6.8(2H); 8(1H) | 1760 |
| MD 280404 | 1 | 0 | 2-OCH₃ | CH=CH₂ | trans | base | C₁₄H₁₅NO₃ | 134 | ¹H | CDCl₃ | 1.4–2.4(2H); 2.8(2H); 3.7(4H); 4.5(1H); 5.2–6.2(3H); 6.6–6.8(2H); 8.1(1H) | 1750 |
| MD 280386 | 1 | 0 | 2-OCH₃ | CH₂OH | cis | base | C₁₃H₁₅NO₄ | 162 | ¹H | DMSOd₆ | 2.1(2H); 2.9(2H); 3.8–4.8(8H); 6.6–6.8(2H); 8(1H) | 1720 |
| MD 280387 | 1 | 0 | 2-OCH₃ | CH₂OH | trans | base | C₁₃H₁₅NO₄ | 147 | ¹H | DMSOd₆ | 2(2H); 2.8(2H); 3.6–4.4(7H); 5.2(1H); 6.6–6.9(2H); 8(1H) | 1720 |
| MD 280448 | 1 | 0 | 2-OCH₃ | CH₂—OCH₃ | cis | base | C₁₄H₁₇NO₄ | 99 | ¹H | CDCl₃ | 2(2H); 2.8(2H); 3.3(3H); 3.6(2H); 3.8(3H); 4.2(1H); 4.7(1H); 6.6–6.8(2H); 8(1H) | 1740 |
| MD 280449 | 1 | 0 | 2-OCH₃ | CH₂—OCH₃ | trans | base | C₁₄H₁₇NO₄ | 105 | ¹H | CDCl₃ | 1.6–2.4(2H); 2.9(2H); 3.4(3H); 3.6–4.4(7H); 6.6–6.8(2H); 8.1(1H) | 1750 |
| MD 370024 | 1 | 0 | 2-OCH₃ | CH₂—NH₂ | cis | salt HCl | C₁₃H₁₇ClN₂O₃ + 6.2% H₂O | >250 | ¹H | DMSOd₆ | 2(2H); 2.8(2H); 3.2(2H); 3.7(3H); 4.3(1H); 5(1H); 6–6.8(2H); 7.9(1H) | 1760 |
| MD 370025 | 1 | 0 | 2-OCH₃ | CH₂—NH₂ | trans | salt HCl | C₁₃H₁₇ClN₂O₃ + 4.8% H₂O | >250 | ¹H | DMSOd₆ | 1.6–2.2(2H); 2.8(2H); 3.3(2H); 3.6(3H); 4(1H); 4.5(1H); 6.6–6.8(2H); 7.9(1H) | 1760 |
| MD 370026 | 1 | 0 | 2-OCH₃ | CH₂—NHCH₃ | cis | HCl | C₁₄H₁₉ClN₂O₃ | >250 | ¹H | DMSOd₆ | 2(2H); 2.6(3H); 2.8(3H); 3.4(2H); 3.7(3H); 4.4(1H); 5.2(1H); 6.1–7(2H); 7.9(1H) | 1750 |
| MD 370027 | 1 | 0 | 2-OCH₃ | CH₂—NHCH₃ | trans | salt HCl | C₁₄H₁₉ClN₂O₃ | >250 | ¹H | DMSOd₆ | 1.6–2.4(2H); 2.6(3H); 2.8(2H); 3.4(2H); 3.7(3H); 4(1H); 4.7(1H); 6.6–6.9(2H); 7.9(1H) | 1750 |
| MD 370028 | 1 | 0 | 2-OCH₃ | CH₂N—(CH₃)₂ | cis | salt HCl | C₁₅H₂₁ClN₂O₃ | >250 | ¹H | DMSOd₆ | 1.6–2.4(2H); 2.8(8H); 3.6(2H); 3.7(3H); 4.4(1H); 5.4(1H); 6.6–6.9(2H); 7.8(1H) | 1740 1760 |
| MD 370029 | 1 | 0 | 2-OCH₃ | CH₂N(CH₃)₂ | trans | salt HCl | C₁₅H₂₁ClN₂O₃ + 5.12% H₂O | >250 | ¹H | DMSOd₆ | 1.5–2.4(2H); 2.8(8H); 3.3–4.1(6H); 4.9(1H); 6.6–6.9(2H); 8(1H) | 1760 |
| MD 370067 | 2 | 0 | H | CH₂OH | cis | base | C₁₃H₁₅NO₃ | 170 | ¹H | DMSOd₆ | 1.1–2.2(4H); 2.5–3(2H); 3.5–4(3H); 4.7(1H); 5.1 | 1730 1750 |

TABLE I-continued (I)

$$R_2 \underset{3}{\overset{2}{\underset{4}{\bigg|}}} \underset{N}{\overset{1}{\bigcirc}} \underset{O}{\overset{(\ )_n}{\underset{O}{\bigg|}}} R_1$$

| Code | n | p | R₂ | R₁ | Configuration | Base or salt | Empirical formula | Mp (°C.) | Nucleus | Solvent | NMR δ p.p.m. | I.R. νC=O cm⁻¹ |
|---|---|---|---|---|---|---|---|---|---|---|---|---|
| MD 370022 | 2 | 0 | 2-OCH₃ | CH₂OH | cis | base | C₁₄H₁₇NO₄ | 120 | ¹H | DMSOd₆ | (1H); 7-7.5(4H) 1-2.2(4H); 2.7(2H); 3.7 (6H); 4.6(1H); 5(1H); 6.6-6.8(2H); 7.2(1H) | 1730 |
| MD 370023 | 2 | 0 | 2-OCH₃ | CH₂OH | trans | base | C₁₄H₁₇NO₄ | 200 | ¹H | DMSO | 1.2-2.2(4H); 2.7(2H); 3.5(3H); 3.7(3H); 4.2(1H); 5(1H); 6.6-6.8(2H); 7.1(1H) | 1730 |
| MD 370317 | 1 | 1 | 2-OCH₃ | CH=CH₂ | least polar | base | C₁₅H₁₇NO₃ | 140 | ¹H | CDCl₃ | 1.2-2.2(4H); 2.8(2H); 3.4-3.7(1H); 3.7(3H); 4.6-4.9(1H); 5.1-6.2 (3H); 6.5-6.9(2H); 7.6(1H) | 1680 |
| MD 370318 | 1 | 1 | 2-OCH₃ | CH=CH₂ | most polar | base | C₁₅H₁₇NO₃ | 106 | ¹H | CDCl₃ | 1.8-2.3(4H); 2.8(2H); 3.4-3.7(1H); 3.7(3H); 4.6-6.3(4H); 6.5-6.9 (2H); 7.8(1H) | 1690 |
| MD 370017 | 2 | 0 | H | CH=CH₂ | cis | base | C₁₄H₁₅NO₂ | 131 | ¹H | CDCl₃ | 1.2-2.3(4H); 2.7(2H); 3.4-3.9(1H); 5-6.3 (4H); 7-7.5(4H) | 1750 |
| MD 370018 | 2 | 0 | H | CH=CH₂ | trans | base | C₁₄H₁₅NO₂ | 95 | ¹H | CDCl₃ | 1-2.3(4H); 2.6-2.9 (2H); 3.1-3.5(1H); 4.6 (1H); 5.1-6.3(3H); 7-7.6(4H) | 1750 |
| MD 370333 | 1 | 0 | 3-Cl | CH=CH₂ | trans | base | C₁₃H₁₂ClNO₂ | oil | ¹H | CDCl₃ | 1.2-2.2(2H); 2.6-3(2H); 3.9-4.4(1H); 5.9-6.2 (4H); 6.8-7.2(2H); 8.2(1H) | 1750 |
| MD 370334 | 1 | 0 | 3-Cl | CH=CH₂ | cis | base | C₁₃H₁₂ClNO₂ | oil | ¹H | CDCl₃ | 1-2.5(2H); 2.7-3.1(2H); 3.5-4(1H); 4.5-4.7(1H); 5.3-6.3(3H); 7(3H); 8.4(1H) | 1750 |
| MD 370240 | 1 | 0 | 3-CH₃ | CH=CH₂ | cis | base | C₁₄H₁₅NO₂ | oil | ¹H | CDCl₃ | 1.2-2.2(2H); 2.3(3H); 2.7-3.1(2H); 3.8-4.4 (1H); 4.9-6.3(4H); 6.7-7.2(2H); 8.0(1H) | — |
| MD 370239 | 1 | 0 | 3-CH₃ | CH=CH₂ | trans | base | C₁₄H₁₅NO₂ | oil | ¹H | CDCl₃ | 1.2-2.4(2H); 2.4(3H); 2.7-3.1(2H); 3.5-4(1H); 4.6(1H); 5.3-6.3(3H); 6.7-7.2(2H); 8.1(1H) | — |
| MD 370250 | 2 | 0 | 2-OCH₃ | CH=CH₂ | cis | base | C₁₅H₁₇NO₃ | 175 | ¹H | CDCl₃ | 1-2.3(4H); 2.5-2.9(2H); 3.4-3.8(1H); 3.8(3H); 5-6.3(4H); 6.6-6.9 (2H); 7.2(1H); | — |
| MD 370251 | 2 | 0 | 2-OCH₃ | CH=CH₂ | trans | base | C₁₅H₁₇NO₃ | 123 | ¹H | CDCl₃ | 1.1-2.3(4H); 2.6-2.9 (2H); 3.1-3.5(1H); 3.7(3H); 4.5(1H); 5.1 -6.3(3H); 6.6-6.9(2H); 7.3(1H) | 1750 |

In table I, Mp means melting point

The compounds of formula (I) and their physiologically acceptable salts have been tested in vitro and in vivo and have been shown to have an interesting therapeutic activity. In particular these compounds and salts have proved active as inhibitors of the monoamine oxydase and capable of potentiating the effects of serotonin when it is administered to animals in the form of the precursor hydroxy-5 tryptophan.

This activity has been demonstrated:

in vitro on homogenates of rat brain, by measuring the concentration of the product inhibiting by 50% ($IC_{50}$) the activity of the monoamine oxydase utilising serotonin as substrate at 480 μM, according to the method described by M. STROLIN BENEDETTI. T. BOUCHER and C. J. FOWLER in Naunyn—Schmiedebergs Archiv. of Pharm. (1983) 323, 315-320;

in vivo by determining in rats the dose of the product which, administered orally, causes in 50% of the animals ($ED_{50}$) the appearance of generalised trembling or stereotypies (finger-tapping as on a piano, movements of the head) following the intraperitoneal administration 1 h after the first treatment of a dose of 120 mg/kg of hydroxy-5 tryptophan (5-HTP) [M. JALFRE, B. BUCHER, A. COSTON, G. MOCQUET, R. D. PORSOLT, Arch. Int. Pharmacodyn., (1982), 259, 194–221].

The activity of some compounds of the invention are given in following Table II for illustrating the invention.

TABLE II

| Compound tested Code No. | Test in vivo $ED_{50}$ (mg/kg/p.o.) | Test in vitro $IC_{50}$ (μm) |
| --- | --- | --- |
| MD 280430 | 105 | 1.4 |
| MD 200682 | 2.3 | 0.09 |
| MD 280404 | 11 | 0.029 |
| MD 200602 |  | 2.8 |
| MD 200718 |  | 8.7 |
| MD 200502 |  | 0.5 |
| MD 200503 | 20 | 0.057 |
| MD 200504 | 7.8 |  |
| MD 280448 | 1.8 | 0.009 |
| MD 280449 |  | 0.006 |
| MD 370024 |  | 1 |
| MD 370025 |  | 1.6 |
| MD 370027 | 5.8 |  |
| MD 280386 |  | 0.019 |
| MD 280387 |  | 0.075 |
| MD 370336 |  | 0.08 |
| MD 370335 |  | 0.097 |

Moreover, no particular toxic signs were noted in the rodent by administration of the compounds according to the invention at the doses at which they demonstrate a pharmacological activity. Thus, for example, the compounds MD 280 449 and MD 370 026 have a $LD_{50}$ in mice respectively of 1120 and 263 mg/kg/p.o.

The above data show the therapeutic interest of the compounds of formula (I) and their physiologically acceptable salts according to the invention. Thus these compounds and salts find their application as medicaments for humans and for animals, particularly for the treatment of depressive states.

The present invention also extends to pharmaceutical or veterinary compositions containing at least one of the said compounds and salts, as well as one or more physiologically acceptable vehicles. These compositions can be formulated with a view to oral administration and then they are presented for example in the form of sugar-coated pills, capsules, tablets or solutions to be drunk, or with a view to parenteral administration and then they are presented as injectable solutions.

Finally, the doses at which the compounds according to the invention can be administrated will depend particularly upon the means of administration, the body weight of the patient, the state of the latter and the therapeutic power of the compounds used. Generally the doses could reach 1 to 50 mg/kg/day, taken in one or more times.

We claim:

1. An oxazoloquinoline compound of the formula:

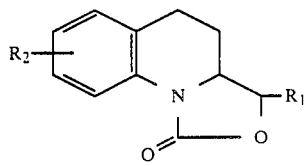

or a pharmaceutically acceptable mineral or organic acid addition salt thereof, wherein:
$R_1$ is a hydrogen atom; a $C_1$-$C_4$ alkyl group; a phenyl group; a $C_2$-$C_3$ alkenyl group; or a methyl group substituted by a hydroxy group, a $C_1$-$C_4$ alkoxy group, an amino group, a N-($C_1$-$C_4$) alkyl amino group or a N,N-di($C_1$-$C_4$) alkylamino group; and
$R_2$ is a hydrogen atom; a halogen atom; a $C_1$-$C_4$ alkyl group or a $C_1$-$C_4$ alkoxy group.

2. A pharmaceutical composition for use as an antidepressant agent comprising a therapeutically effective amount of an oxazoloquinoline compound or acid addition salt thereof of claim 1 and a pharmaceutically acceptable carrier.

3. A method for the treatment of depressive states in humans or animals, which comprises administering to a human or animal in need of such treatment an effective amount of an oxazoloquinoline compound or acid addition salt thereof of claim 1.

4. The compound of claim 1, wherein $R_1$ is a methoxymethyl group and $R_2$ is a 2-methoxy group.

5. The compound of claim 1, wherein $R_1$ is a hydroxymethyl group and $R_2$ is a 2-methoxy group.

6. The compound of claim 1, wherein $R_1$ is a methoxymethyl group and $R_2$ is a hydrogen atom.

7. The compound of claim 1, wherein $R_1$ is a methylaminomethyl group and $R_2$ is a 2-methoxy group.

8. The compound of claim 1, wherein $R_1$ is a ethenyl group and $R_2$ is a 2-methoxy group.

* * * * *